United States Patent
Blanzy

(10) Patent No.: US 9,987,121 B2
(45) Date of Patent: Jun. 5, 2018

(54) METHOD OF MAKING AN ENDOPROSTHESIS CONTAINING MULTI-PHASE STAINLESS STEEL

(71) Applicant: W. L. Gore & Associates, Inc., Newark, DE (US)

(72) Inventor: Jeffrey S. Blanzy, Flagstaff, AZ (US)

(73) Assignee: W. L. Gore & Associates, Inc., Newark, DE (US)

( * ) Notice: Subject to any disclaimer, the term of this patent is extended or adjusted under 35 U.S.C. 154(b) by 566 days.

(21) Appl. No.: 14/543,085

(22) Filed: Nov. 17, 2014

(65) Prior Publication Data

US 2015/0164633 A1 Jun. 18, 2015

Related U.S. Application Data

(63) Continuation of application No. 13/167,547, filed on Jun. 23, 2011, now Pat. No. 8,888,838, which is a (Continued)

(51) Int. Cl.
*A61F 2/06* (2013.01)
*A61F 2/07* (2013.01)
(Continued)

(52) U.S. Cl.
CPC .................. *A61F 2/07* (2013.01); *A61C 7/20* (2013.01); *A61F 2/90* (2013.01); *A61F 2/958* (2013.01);
(Continued)

(58) Field of Classification Search
CPC .... A61F 2/07; A61F 2/90; A61F 2/958; A61F 2002/9522; A61F 2240/001; A61F 2/91; C22C 38/02; C22C 38/04; C22C 38/58; C22C 38/44; C22C 38/001; A61C 7/20; A61L 31/022; A61L 27/042; A61L 29/02; C21D 6/004; C21D 9/0068; C21D 1/56; C21D 2211/001; C21D 9/08; C21D 1/26; C21D 2211/005; Y10T 29/49863
See application file for complete search history.

(56) References Cited

U.S. PATENT DOCUMENTS 3,807,991 A 4/1974 Gregory et al.
4,820,485 A 4/1989 Ototani et al.
(Continued)

FOREIGN PATENT DOCUMENTS

EP 0339004 4/1989
JP H2-17072 1/1990
(Continued)

OTHER PUBLICATIONS

Younkin, CN. Multiphase MP35N Alloy for Medical Implants. J. Biolmed. Mater. Res. Symposium 1974; 5 (part 1):219-226.
(Continued)

*Primary Examiner* — Jun Yoo

(57) ABSTRACT

An endoprosthesis fabricated from multi-phase ferrous steel. Endoprostheses can include a variety of devices such as staples, orthodontic wires, heart valves, filter devices, and stents, many of which devices are diametrically expandable devices. Multi-phase ferrous steels include dual phase steels and transformation induced plasticity steels (TRIP steels).

5 Claims, 21 Drawing Sheets

Related U.S. Application Data continuation of application No. 12/981,102, filed on Dec. 29, 2010, now abandoned.

(60) Provisional application No. 61/291,497, filed on Dec. 31, 2009.

(51) Int. Cl.

| | | |
|---|---|---|
| *A61C 7/20* | (2006.01) | |
| *A61L 27/04* | (2006.01) | |
| *A61L 29/02* | (2006.01) | |
| *A61L 31/02* | (2006.01) | |
| *C21D 1/56* | (2006.01) | |
| *C21D 6/00* | (2006.01) | |
| *C21D 9/00* | (2006.01) | |
| *C22C 38/00* | (2006.01) | |
| *C22C 38/44* | (2006.01) | |
| *A61F 2/90* | (2013.01) | |
| *A61F 2/958* | (2013.01) | |
| *C22C 38/02* | (2006.01) | |
| *C22C 38/04* | (2006.01) | |
| *C22C 38/58* | (2006.01) | |
| *A61F 2/91* | (2013.01) | |
| *C21D 1/26* | (2006.01) | |
| *C21D 9/08* | (2006.01) | |
| *A61F 2/95* | (2013.01) | |

(52) U.S. Cl.
CPC .............. *A61L 27/042* (2013.01); *A61L 29/02* (2013.01); *A61L 31/022* (2013.01); *C21D 1/56* (2013.01); *C21D 6/004* (2013.01); *C21D 9/0068* (2013.01); *C22C 38/001* (2013.01); *C22C 38/02* (2013.01); *C22C 38/04* (2013.01); *C22C 38/44* (2013.01); *C22C 38/58* (2013.01); *A61F 2/91* (2013.01); *A61F 2002/9522* (2013.01); *A61F 2230/0069* (2013.01); *A61F 2240/001* (2013.01); *C21D 1/26* (2013.01); *C21D 9/08* (2013.01); *C21D 2211/001* (2013.01); *C21D 2211/005* (2013.01); *Y10T 29/49863* (2015.01)

(56) References Cited

U.S. PATENT DOCUMENTS

| | | | |
|---|---|---|---|
| 4,964,924 A | 10/1990 | Hagenfeldt et al. | |
| 4,964,925 A | 10/1990 | Hagenfeldt et al. | |
| 5,055,018 A | 10/1991 | Ototani | |
| 5,268,141 A | 12/1993 | Ototani et al. | |
| 6,187,261 B1 | 2/2001 | Fedchun | |
| 6,206,911 B1* | 3/2001 | Milo | A61F 2/91 623/1.15 |
| 6,327,772 B1 | 12/2001 | Zadno-Azizi et al. | |
| 6,391,253 B1 | 5/2002 | Tochihara et al. | |
| 6,582,652 B2 | 6/2003 | Craig | |
| 6,689,162 B1* | 2/2004 | Thompson | A61F 2/06 623/1.18 |
| 7,445,749 B2 | 11/2008 | Craig | |
| 7,455,811 B2 | 11/2008 | Sjodin | |
| 7,491,910 B2 | 2/2009 | Kapoor et al. | |
| 8,287,805 B2 | 10/2012 | Sjodin | |
| 8,591,672 B2* | 11/2013 | Janko | A61L 31/022 148/320 |
| 8,888,838 B2 | 11/2014 | Blanzy | |
| 2002/0138134 A1 | 9/2002 | Kim | |
| 2003/0091458 A1 | 5/2003 | Weber et al. | |
| 2003/0103860 A1 | 6/2003 | Qiao | |
| 2003/0165394 A1 | 9/2003 | Kloss-Ulitzka | |
| 2004/0044399 A1* | 3/2004 | Ventura | A61F 2/91 623/1.16 |
| 2004/0056074 A1 | 3/2004 | Sjodin | |
| 2005/0182478 A1* | 8/2005 | Holman | C21D 10/005 623/1.15 |
| 2006/0130934 A1* | 6/2006 | Kuroda | A61B 17/0057 148/221 |
| 2006/0204738 A1* | 9/2006 | Dubrow | A61F 13/02 428/292.1 |
| 2008/0199345 A1 | 8/2008 | Scheller et al. | |
| 2009/0162238 A1 | 6/2009 | Bergstrom et al. | |
| 2009/0198320 A1 | 8/2009 | Mueller et al. | |
| 2010/0174367 A1 | 7/2010 | Janko et al. | |
| 2012/0279881 A1 | 11/2012 | Janko et al. | |

FOREIGN PATENT DOCUMENTS

| | | | |
|---|---|---|---|
| JP | 05-247592 | 9/1993 | |
| JP | 09-310157 | 12/1997 | |
| JP | 2005-507459 | 3/2005 | |
| WO | WO 02078763 A1 * | 10/2002 | ........... A61L 31/022 |
| WO | 03/038136 | 5/2003 | |
| WO | 2011/082280 | 7/2011 | |

OTHER PUBLICATIONS

Syrett BC, Davis EE. Crevice Corrosion of Implant Alloys—A Comparison of In-Vitro and In-Vivo Studies. American Society for Testing and Materials 1979 229-244.

Syrett BC, Davis EE. In Vivo Evaluation of a High-Strength, High-Ductility Stainless Steel for Use in Surgical Implants. Journal of Biomedical Materials Research, 1979 13:543-556.

\* cited by examiner

METHOD OF MAKING AN ENDOPROSTHESIS CONTAINING MULTI-PHASE STAINLESS STEEL

FIELD OF THE INVENTION

The present invention relates to the field of endoprostheses, and particularly to the field of diametrically expandable endoprostheses.

BACKGROUND OF THE INVENTION

Various types of metallic materials have been used in implanted medical devices in the past. Type 316L or a 316LVM stainless steel, cobalt-chromium alloys, commercially pure titanium, and titanium alloys are typical metals used for implantable devices. The environment and method of implantation dictates the use of certain raw materials with specific biocompatibility and material properties. These materials typically possess the necessary physical properties such as tensile strength, fatigue resistance, elastic recoil and yield strength for specific applications.

It is often desirable to form these metallic materials into complex shapes (including diametrically expandable shapes) such as artificial heart valves, stents, and filters. These types of applications would typically require a metallic material with strength properties close to that of 316L or a 316LVM stainless steel as well as an elastic recoil similar to 316L or a 316LVM. There are often applications that require that these complex shapes be expanded in size (e.g., via a balloon) to conform or comply with certain geometry, be that anatomical or device-driven geometry. In these applications, the metallic material selected would have a relatively low yield strength to allow ease of expansion. The intended environment of implantation of some of these devices (e.g., coronary stents) typically requires a metallic material with a relatively high strength.

Device geometry, method of delivery and environment often force the choice of a metallic material that compromises in one of the four important physical property areas: tensile strength, fatigue resistance, elastic recoil or yield strength. For these reasons, the choice of a metallic material for a particular application is often challenging and compromising.

In relation to other advanced high-strength steels, multiple phase steels (i.e., multi-phase steels) exhibit better ductility at a given strength level. In an example of one multiple phase steel, dual phase steel, the enhanced formability stems from the combination of ferrite and martensite phases present in the raw material. Dual phase steel has a high work hardening rate that enables it to behave in a stable manner during a stamping or forming process. Dual phase steel may be purchased from a supplier such as AK Steel (West Chester, Ohio).

In another example of multiple phase steels, TRIP (Transformation Induced Plasticity) steel, enhanced formability comes from the transformation of retained austenite (ductile, high temperature phase of iron) to martensite (tough, non-equilibrium phase) during plastic deformation. Enhanced formability also stems from a high work hardening rate, which enables the metal to behave in a stable way during a stamping or forming process. Because of this increased formability, TRIP steel may be used to produce more complex shapes than other high strength steels. TRIP steel may be purchased from suppliers such as US Steel (Pittsburgh, Pa.) or ArcelorMittal (Brazil).

TRIP steel containing 4% Mo has been evaluated against type 316L or a 316LVM stainless steel and cast Vitallium alloy as a potential material for use as an implantable material for orthopedic applications. Results from in vivo evaluation of TRIP steel versus 316L stainless steel in these applications showed that TRIP steel was susceptible to stress-corrosion cracking and much more susceptible to crevice corrosion.

SUMMARY OF THE INVENTION

A first embodiment provides an endoprosthesis (i.e., a prosthesis that is placed internally within a body) comprised of a multi-phase (multiple phase) ferrous stainless steel. Multi-phase ferrous stainless steel (also referred to as Advanced High Strength Steel, or AHSS) is defined as any ferrous steel with more than one phase (e.g., austenite, ferrite, banite or martensite) present in the microstructure. Multi-phase ferrous stainless steel will encompass such steels as dual phase, complex phase (more than two phases present in the microstructure), duplex, TRIP, TWIP (Twinning Induced Plasticity) and Q&P (Quenched and Partitioned).

A second embodiment provides a method of making an endoprosthesis comprising the steps of forming (e.g., stamping, wire winding or laser cutting) a multiphase steel material such as TRIP stainless steel into a desired shape, forming the desired shape into a tubular form and crimping (e.g., affixing/securing) said tubular form onto a balloon-based endovascular delivery system, delivering said desired shape to an area of treatment, and expanding said desired shape at the area of treatment by inflation of the balloon.

DETAILED DESCRIPTION OF THE INVENTION

Figure 1:
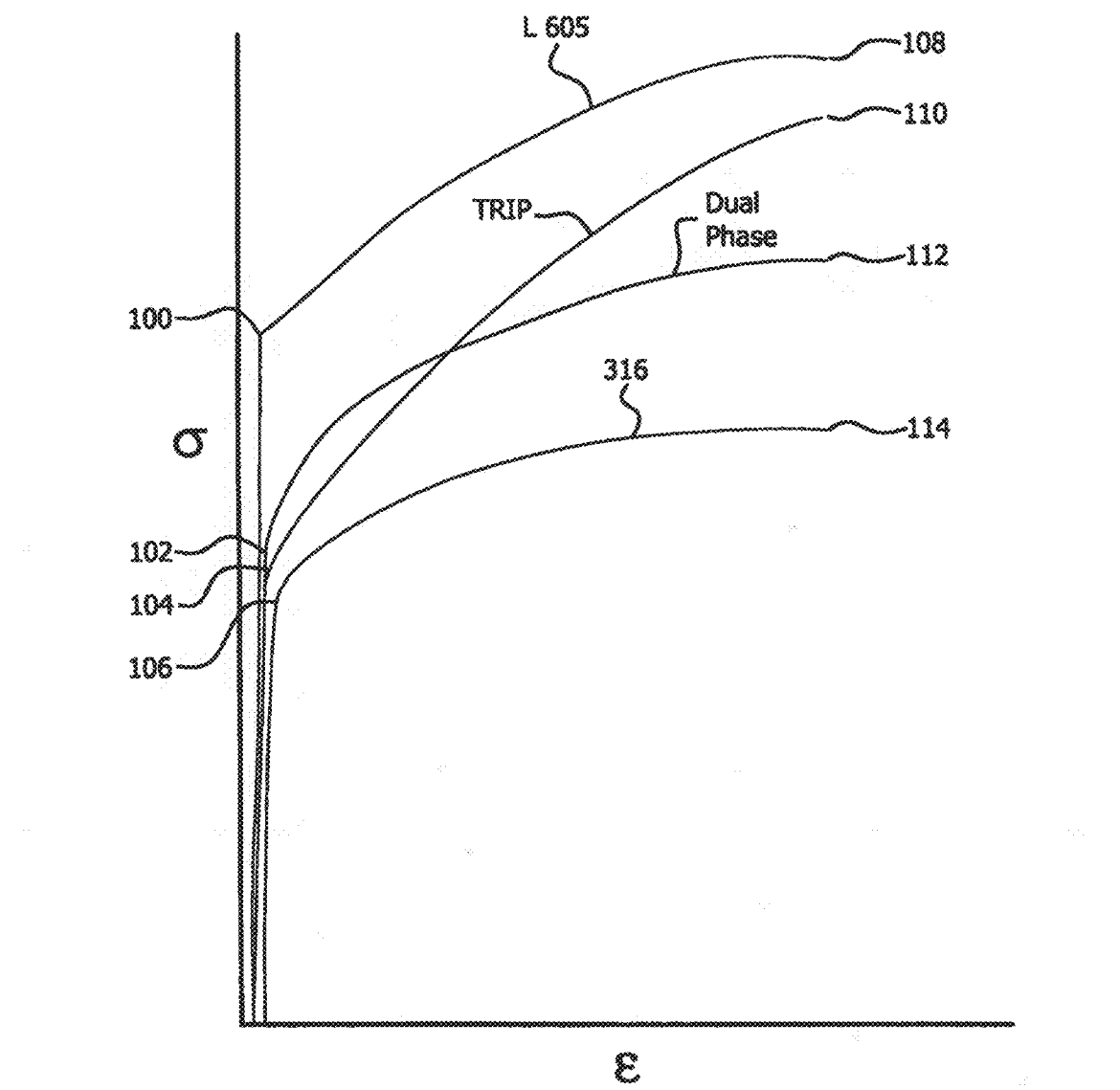
FIG. 1 illustrates a stress-strain curve for L605, 316L or a 316LVM, dual phase steel and TRIP steel.

FIG. 1 illustrates a stress-strain curve comparing the typical properties of a L605 cobalt chromium alloy, a dual phase steel, a TRIP steel, and a 316L or a 316LVM stainless steel. As shown in the figure, L605 has a relatively high yield strength (YS) 100 and a high ultimate tensile strength (UTS) 108 while 316L or a 316LVM has a lower yield strength 106 and a lower ultimate tensile strength 114. Dual phase steel (102) and TRIP steel (104) have a yield strength that is typically lower than that of L605 (100) which enhances formability and ease of expansion. It is noteworthy that the ultimate tensile strength of dual phase steel (102) and TRIP steel (104) are higher than the ultimate tensile strength of 316L or 316LVM (114).

Figure 2:
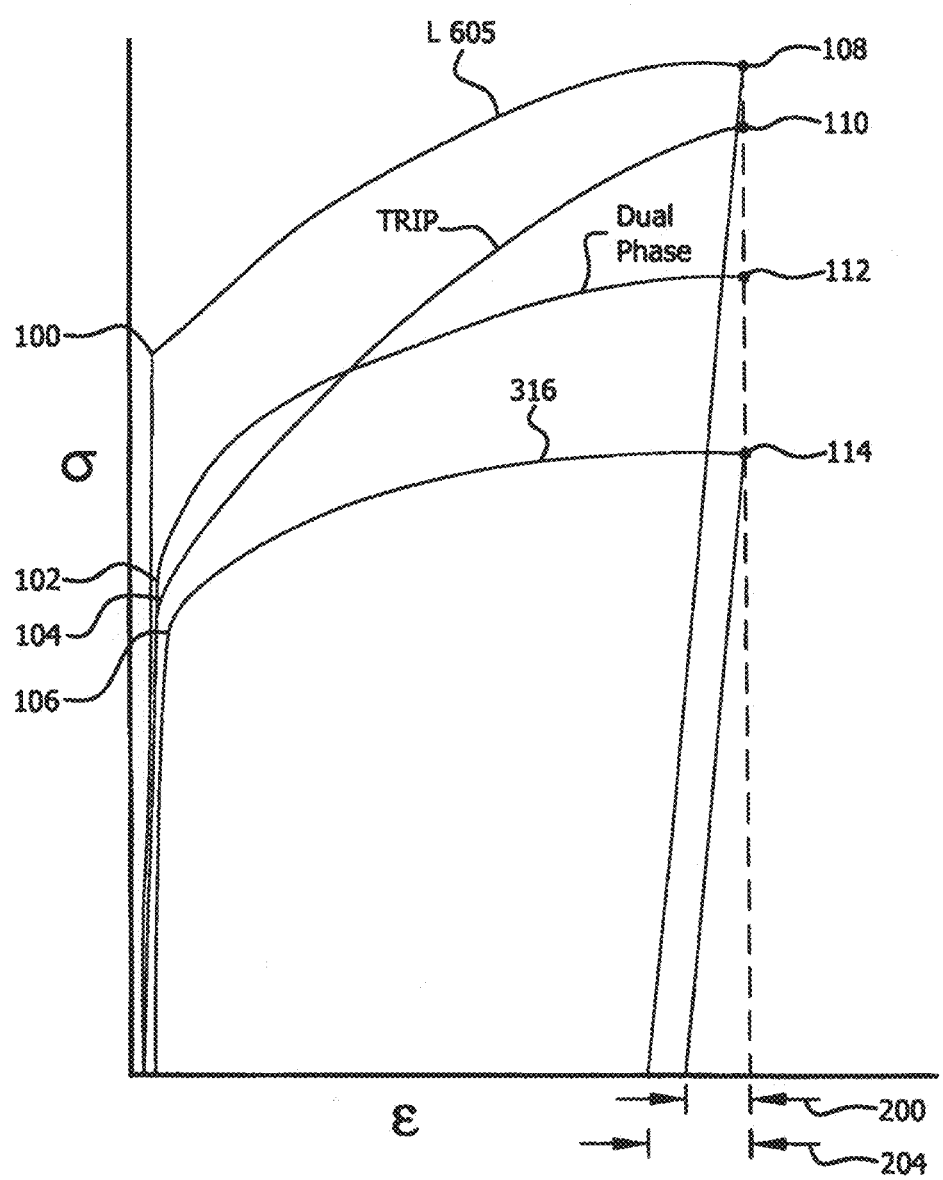
FIG. 2 is a graph showing change in recoil of L605, 316L or a 316LVM

FIG. 2 shows stress-strain curves with change in recoil indicated for typical L605 and 316L or a 316LVM steels used in endoprostheses. The change in recoil for a 316L or a 316LVM steel is shown as strain amount 200 while the change in recoil for a L605 is shown as strain amount 204. The strain amount 204 shows a typical recoil amount for a high modulus, high yield strength metal such as L605. Strain amount 200 shows a typical recoil amount for a low modulus, low yield strength metal such as 316L or a 316LVM. Change in recoil in a dual phase or TRIP steel would fall between the two values. The advantages of a material for use as an endoprosthesis that exhibits the relatively small amount of recoil as that of a 316L or a 316LVM while maintaining the high ultimate tensile strength and a high modulus of L605 would be advantageous.

MRI (Magnetic Resonance Imaging) compatibility is an important property in any metal chosen for an implantable prosthesis. Duplex Stainless steels present a fine microstructure of paramagnetic austenite and ferromagnetic ferrite with a microstructure ratio that typically is around 50% for each phase. Stainless steels like 316 LVM are considered to be MRI compatible because they have a microstructure that is 100% austenite and thus paramagnetic. Materials like plain carbon steels have a ferrite microstructure and are ferromagnetic. Ferromagnetic materials not considered MRI-safe or MRI-compatible due to the fact that they are strongly influenced by magnetic fields. It has been shown that the volume fraction of ferrite can be reduced in Duplex stainless steel through heat treatment. For example, Duplex steel samples have been heat treated in a vacuum furnace to a temperature of 1300° C. and then slowly cooled (inside of the furnace) to 1000° C. and next removed from the furnace and air cooled to room temperature. This processing technique decomposed the ferrite volume fraction in the microstructure from 50% to about 11% without the formation of any secondary brittle sigma phase. Such a sample was then tested using thermomagnetic analysis and was shown to have a very poor ferromagnetic signal due to the low content of ferrite. The thermomagnetic curve was considered to be typical of a paramagnetic material.

A first embodiment provides an endoprosthesis comprised of a multi-phase ferrous steel. These multi-phase ferrous endoprostheses may be fabricated by known means (some of which are described below) as used for such devices made from conventional materials. An example of such an endoprosthesis would be that of a coronary stent. Typically, coronary stents are produced using either a cobalt chromium alloy for post deployment strength, or a 316L or a 316LVM stainless steel for conformability, trackability, minimal elastic recoil, and ease of formability. Stents made from any of these metals are frequently produced with complex geometrical designs. The designs are typically formed using a variety of methods. Some designs are formed from metallic wire into a generally tubular shape. More complex designs are either cut from a thin flat sheet of metal and then bent to form a tube from the cut design or cut directly from a thin tubular form. Either method may then be diametrically compacted to allow the stent to be secured to a balloon catheter. Cutting of the pattern may take place by a variety of means commonly known in the art including but not limited to electrical discharge machining, chemical etching, stamping, or laser cutting. Due to the unique mechanical stresses placed on a coronary stent during manufacture and during delivery of the stent to the desired implant site, the metallic material most widely used is 316L or a 316LVM stainless steel. Typically, these pre-cut metals used to make commercially available coronary stents are excessively thick due to the mechanical demands placed on the deployed device. The properties of multi-phase ferrous steels would allow these same devices to be made with thinner walls while still offering good strength properties.

Coronary stents are typically delivered percutaneously to the desired implant site by attachment onto the outside of a balloon catheter. The catheter carrying the stent is maneuvered through the vasculature of a patient, which is often complex and tortuous. If the metallic material chosen for the stent possesses high strength characteristics, such as cobalt chromium alloy, its ability to successfully navigate the tortuous anatomy may be compromised and upon deployment it will exhibit an inherent recoil. Given the environment of implantation and mechanical needs of a coronary stent, the use of a multiple phase steel would more ideally meet the demands placed on the stent design during formation, delivery and post deployment and rectify many of the aforementioned compromises.

Figures 3A, 3B:
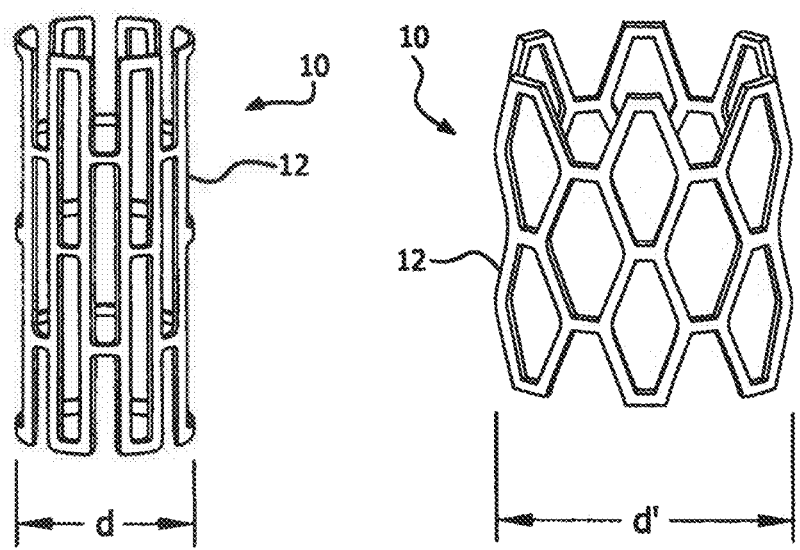
FIGS. 3A and 3B are perspective views of one embodiment of multi-phase ferrous stainless steel endoprosthesis before and after diametrical expansion.

FIGS. 3A and 3B are perspective views of one embodiment of multi-phase ferrous stainless endoprostheses 10 (e.g., stent 12) before and after diametrical expansion, with the diameter difference indicated in the respective figures as d and d'.

Figure 4:
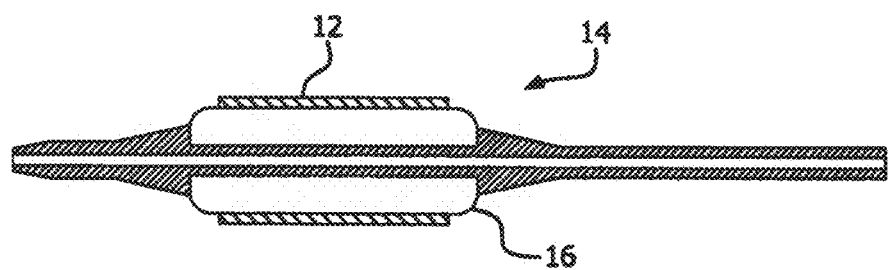
FIG. 4 shows a longitudinal cross sectional view of a multi-phase ferrous stainless steel endoprosthesis mounted on and diametrically expanded by a typical balloon delivery system.

FIG. 4 shows a longitudinal cross sectional view of a multi-phase ferrous stainless steel endoprosthesis 10 (e.g., stent 12) mounted on and diametrically expanded by an inflated catheter balloon 16, all part of a typical balloon delivery system 14.

A further example of an endoprosthesis would be that of a renal stent which may be formed in the same manner and basic shapes as the coronary stent described above. Most renal stents are constructed with two distinct sections, the ostial lesion region and the distal section, to comply with different anatomical demands. The ostial region of a renal stent has high radial strength requirements and is usually constructed with a thicker wall and more longitudinal connectors. The distal portion of a renal stent is desired to be more flexible than the ostial region and is usually constructed with a thinner wall and fewer connectors. The entire stent is desired to be low profile for optimal trackability, accurate placement and must be designed to inflate quickly and easily so as not to block the arteries for any length of time. These conflicting design requirements dictate a compromise in material choice. Most available renal stents are made from 316L or a 316LVM stainless steel. As with other stents and frames discussed above, 316L or a 316LVM allows greater trackability, formability and minimal elastic recoil. In order to achieve these performance goals, the stent must be designed in two distinct sections which increases manufacturing difficulty.

If a multiple phase steel were used, the design could be made homogenous without compromising the needed attributes of high radial strength, flexibility, trackability, and ease of balloon expansion. The design could be made with a thin wall and fewer connectors throughout.

Various other types of diametrically expandable stents may benefit from the use of multi-phase ferrous steels for their manufacture. These can include stents for peripheral, carotid, brain (neural), biliary, hepatic, aortic and thoracic applications. Again, these may be fabricated by known methods. Any or all of these types of stent devices may be provided as stent-grafts wherein the stent frame is given a partial or entire covering (on either the outer, inner or both surfaces of the stent) of a prosthetic graft material such as dacron or ePTFE (expanded polytetrafluoroethylene).

Figure 5:
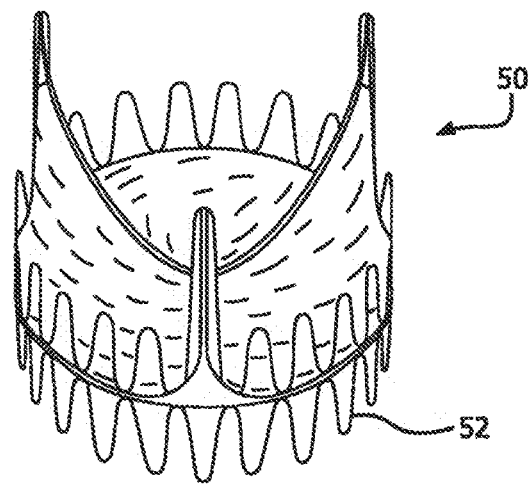
FIG. 5 is a perspective view of one embodiment of an endovascular delivered balloon expandable multi-phase ferrous stainless steel heart valve.
Figure 6:
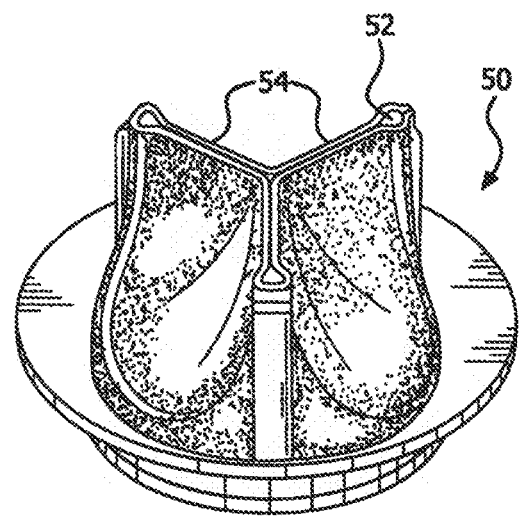
FIG. 6 shows a perspective view of one embodiment of a surgically implantable heart valve containing multi-phase ferrous stainless steel.

A further example of an endoprosthesis would be that of a transcatheter-delivered prosthetic heart valve 50 like those shown in FIGS. 5 and 6. Transcatheter delivered heart valves are typically made from a frame of medical grade stainless steel chosen for the material's formability, trackability characteristics, and minimal elastic recoil. It is also possible to make them from a cobalt nickel or cobalt chromium alloy chosen for the material's mechanical strength. These transcatheter delivered heart valves are deployed directly to the sight of an existing malfunctioning heart valve therefore they take up space that could be otherwise utilized for blood flow. Methods for forming a heart valve frame 52 are similar to those used to form a stent and have been discussed previously. Designs for a frame 52 are often ring-shaped and formed of rows of zig-zag or sinusoidal type undulations (FIG. 5) with longitudinal connectors between the rows. Alternately, they may be formed of diamond shaped elements connected together to form rings. Many other shapes may be envisioned for the frame 52 of a transcatheter-delivered heart valve 50.

Frame 52 has attached a valve material. Materials for a valve 54 could be homografts (donor graft), autografts (typically via the Ross procedure), heterograft or xenograft (animal tissue grafts from most commonly, bovine or porcine donors), or of any biocompatible material such as PTFE (polytetrafluoroethylene) or ePTFE (expanded polytetrafluoroethylene). These materials may be attached to the frame with a variety of methods commonly know in the art such as suturing directly to the frame or suturing to a skirt of another material (e.g., Dacron® or polyester) and then suturing or chemical bonding to the frame.

These heart valves 50 are deployed by a balloon catheter in two methods: transapically or transfemorally; the most common route of delivery is transfemorally. This method of delivery demands the ability of the device attached to a balloon catheter to be flexible enough to track through a considerable length of potentially tortuous anatomy. This trackability demand often dictates the use of a medical grade stainless steel for the heart valve frame.

If the typical medical grade stainless steel is chosen for the frame 52 of a heart valve 50, frame 52 must be somewhat thicker than if a stronger material were chosen such as a cobalt chromium alloy or a cobalt nickel alloy. The mechanical stresses imparted to a valve frame 52 are considerable in the environment of a beating heart. The use of a cobalt alloy would hinder the typical method of delivery of the device as well as render the deployment less accurate. In other words, a thinner frame is desirable to facilitate blood flow and device delivery but the frame must be sufficiently strong to hold up under the mechanical stresses imparted by a beating heart. Multiple phase steel would meet the unique mechanical demands of transcatheter delivered heart valves.

Surgical staples or sternal closure devices may also be beneficially made from multi-phase ferrous steels. Staples are often used to close bowel, lung and skin wounds.

Figure 7:
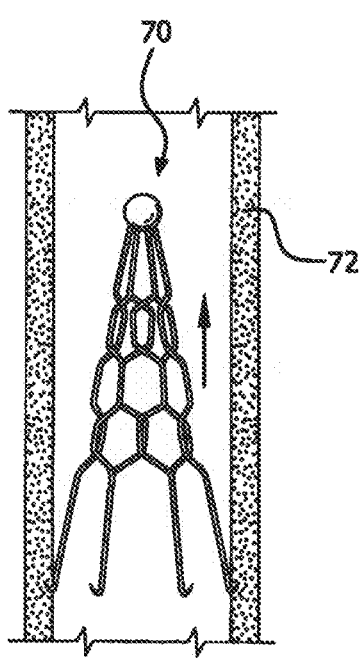
FIG. 7 shows a side view of an implantable filter device.

Implantable filters 70 such as shown by FIG. 7 as implanted in a blood vessel 72 may also be effectively manufactured from the multi-phase ferrous stainless steels described herein. These filters can include inferior vena cava filters and embolic filters. Filters for these applications are often made to be diametrically expandable to allow for insertion into a body conduit for subsequent expansion at a desired site.

Other medical applications for duplex stainless steels would be in the arena of medical leads. Medical pacing leads have an electrical connector component which has a compressible portion that expands to accept an inserted lead and then contracts or is crimped around the lead to provide both an electrical and a spring-like mechanical connection to the lead. Ideally, this crimp connection would be very thin and flexible until the crimp is made but of sufficient strength to withstand the high tensile forces imparted to the lead during implant and explantation. A material such as duplex stainless steel would be an optimal choice for such an application.

Guidewires may also be manufactured from multi-phase ferrous steels.

Orthodontic prosthetics, in particular arch wires, are another application for multi-phase ferrous metals. Arch wires must be able to be formed with very little force but must exert a constant force (chosen by the dentist to be sufficient to cause tooth movement but not painful) over a strain range of up to 5%. This constant force must be maintained without much recoil. Since the load may be applied mechanically, a material that is strong and easily formable would be desirable.

Additional processing steps may be added to the fabrication of any of the above-mentioned devices. For example, a fatigue-life improvement step could be added after forming a device shape. This step may involve pre-straining selected portions of the formed device, electro-polishing the formed device, or media blasting the formed device to impart compressive residual stresses at the surface of the metal. If the multi-phase ferrous metal were to be supplied with an annealed surface, this processing step could be performed prior to device formation. A further processing step could also be added to improve bonding strength for coating or cover adhesion. This step is similar to that for fatigue life improvement but results in improving bonding life. As with fatigue life improvement, this step could be performed either prior to or following device formation depending on the raw material provided.

Endoprostheses as described above may be provided with coatings of a variety of types of bioactive substances (therapeutic agents), such as blood thinners or antibiotics. These may be bonded to such devices by a variety of known methods appropriate to the desired bioactive agent. They may also be optionally coated with various polymers, optionally containing therapeutic agents, as desired for specific applications. Suitable coatings may include fluoropolymers such as fluorinated ethylene propylene (FEP), polytetrafluoroethylene (PTFE), ePTFE and copolymers of tetrafluoroethylene and polyalkylvinylethers such as polyalkylmethylether (TFE/PMVE).

EXAMPLES

Example 1

Figure 8:
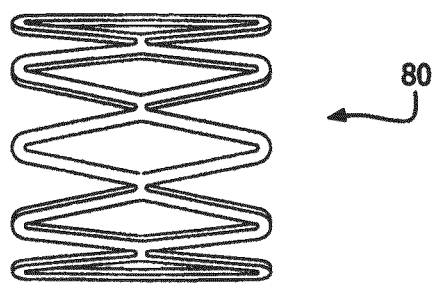
FIG. 8 shows a side view of an alternative balloon expandable stent made from a multi-phase ferrous steel.

FIG. 8 shows a balloon expandable tubular endoprosthesis 80 of an exemplary type that may be made from multi-phase ferrous steel. For clarity, only the side of the device closest to the viewer is shown in FIG. 8, with the back side of the tubular form (furthest from the viewer) omitted, as such a device would generally appear to a viewer if a mandrel or other cylindrical form were inserted into the interior of the tubular form of the device. FIG. 8 illustrates the endoprosthesis 80 as it would appear following partial diametrical expansion with a catheter balloon. A device of this type was manufactured using Duplex Grade S2205 (available from Sandmeyer Steel Co., Philadelphia, Pa.) in the form of a steel plate of 6.35 mm thickness. The steel plate as received had the following properties:
  UTS of 845 MPa
  0.2% YS of 644 MPa
  Elongation (%) of 29
  Volume fraction of austenite of 56.4% and ferrite of 43.6%.

The volume fraction of austenite and ferrite was measured using x-ray diffraction techniques with a copper source. The measurements were made in the center of the plate where the plate was cross-sectioned.

The steel plate was heat treated at 1300° C. and furnace cooled to 1000° C. After reaching 1000° C. the plate was cooled in ambient air to room temperature. The steel plate following heat treatment had the following properties:
  UTS of 781 MPa
  0.2% YS of 485 MPa
  Elongation (%) of 34
  Modulus of 216 GPa
  Volume fraction of austenite of 41.4% and ferrite of 58.6%.

Tensile testing was done in accordance with ASTM E8. Tensile samples from the heat-treated stainless steel plate were machined into threaded tensile bars. Laser cut tensile strips were cut from the 316LVM and L605 tubing and also tested in tension. The mechanical properties of the 316 LVM were as follows:
  UTS of 661 MPa
  0.2% YS of 340 MPa
  Elongation (%) of 53
  Modulus of 126 GPa The mechanical properties of the comparative L605 samples tested were as follows:
  UTS of 1079 MPa
  0.2% YS of 567 MPa
  Elongation (%) of 56
  Modulus of 235 GPa This testing showed that the heat-treated Duplex stainless steel has a modulus of elasticity, yield strength, and ultimate tensile strength that are between the two alloys while the total elongation is less then 316LVM and L605.

After heat treatment, hypotubes were wire EDM (Electrical Discharge Machine) machined (Mitsubishi Wire EDM, model FA205) from the steel plate. These hypotubes had an outer diameter of 4.57 mm and a wall thickness of 0.254 mm. Since the EDM tubes were too small in length to be laser cut, stainless steel tube extenders were made and press fitted into the ends of the hypotubes. Stent rings of the type shown in FIG. 8 were then laser cut from the hypotubes; diameter and wall thickness were not affected. Laser cutting was performed at the expanded diameter of the endoprosthesis (i.e., the diameter the device would have following typical balloon expansion of the device), so that the appearance was generally as shown by FIG. 8. Laser cut stent rings of the same type and the same dimensions were made from 316LVM alloys. The Duplex rings and the 316LVM alloy rings underwent a simulated crimp to 1.5 mm. The rings were then radially expanded using a tapered mandrel to 10 mm and put into the Blockwise J-crimper (Model RJAT, Blockwise Engineering LLC, Phoenix, Ariz.). The J-crimper was mounted into an Instron tensile tester (Model 5564, Instron Corp., Norwood, Mass.) and the rings were individually placed into the mechanical iris. The rings were then individually diametrically crushed in the iris to an intermediate size (1.65 mm outside diameter) and the strength of the rings was determined with the Instron Bluehill software. The Duplex ring was shown to be about 20% stronger than the 316LVM rings.

Recoil of the Duplex laser cut rings was measured using the following process. Endoprosthesis rings (stent rings) of the type described above were fabricated of the heat-treated Duplex S2205 steel, and of both 316LVM, and L605 similar to that described previously. These rings were diametrically expanded using a tapered stainless steel mandrel having a maximum diameter 12.80 mm cylindrical end portion. The rings were expanded to an inner diameter of 12.80 mm and then removed from the tapered mandrel. These 12.80 mm diameter was considered functionally relevant for stent rings of this design. Following diametrical expansion and removal from the tapered mandrel, the inner diameter of each ring was measured using a Nikon vision system (Model VMR 3020 type 3). The diameter of each ring was measured at ten different locations evenly spaced around the inner diameter of the stent and averaged. These measurements demonstrated a recoil of 0.051 mm in the 316LVM stent ring, 0.152 mm in the Duplex steel stent ring, and 0.279 mm in the L605 stent ring. These data indicate that the L605 ring has a higher degree of elastic recoil as compared to the heat-treated Duplex ring as is therefore less formable.

Figure 9:
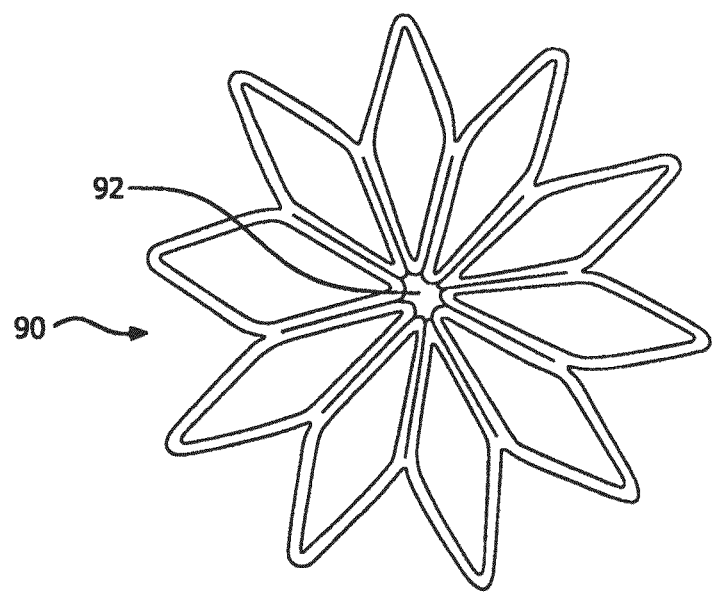
FIG. 9 shows a view of the stent of FIG. 8 as made from a sheet of multi-phase ferrous steel.

In addition to being machined from a billet as generally described above, stent rings of the type shown by FIG. 8 may also be machined from sheet materials. A machined pattern 90 for such a stent is shown in FIG. 9. Following machining of the sheet, the resulting planar form 90 is then shaped into a tube using a tapered mandrel. The small diameter of the mandrel must be capable of being inserted into the center opening 92 of planar form 90. The mandrel should have a maximum diameter equal to the intended inside diameter of the partially expanded stent form; this maximum diameter would include an equal diameter adjacent cylindrical section. Inserting the small end of the mandrel into the center opening 92 of planar form 90 and pushing the mandrel entirely through the planar form 90 results in a tubular form 80 as shown in FIG. 8.

Figure 10:
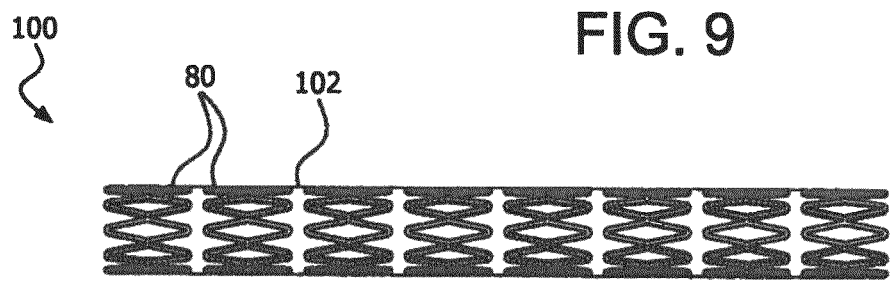
FIG. 10 shows a stent-graft utilizing multiple balloon expandable stents of the type described by FIG. 8.

Multiple stent rings were made as described above made from the heat-treated Duplex S2205 steel. Eight rings 80 were joined to the outer surface of a graft material such as the ePTFE tube 102 to create a stent-graft 100 as shown in FIG. 10. The manufacture of stent-grafts of this type is described in US Published Patent Application No. 2008/0119943, incorporated by reference herein. The resulting balloon expandable stent-graft 100 of approximately 40 mm length could be loaded onto a balloon catheter for subsequent delivery into the vasculature of a patient and subsequent balloon expansion. It is appreciated that the stent-graft 100 shown in FIG. 10 is exemplary only and that many forms of stent-grafts incorporating stents made of multi-phase ferrous steel are possible. It is likewise appreciated that the stent may be joined to the outer surface of the graft material, the luminal surface of the graft material or may be sandwiched between inner and outer layers of graft material. Further, the graft material may incorporate perforations if desired for particular applications such as biliary therapy.

Example 2

While the Duplex S2205 stainless steel alloy, particularly when heat-treated as described above, has been shown to offer good strength capabilities and good forming capabilities for the manufacture of balloon expandable endoprostheses, it is believed that even better alloys are possible for medical devices and particularly expandable endoprostheses. Table 1 shows the composition of one such alloy. It is appreciated that small deviations from this composition may also offer some improvement over the Duplex S2205 alloy.

TABLE 1

Blanzium Composition

| Element | Blanzium (BX-1) wt % |
|---|---|
| C | 0.03 max |
| Mn | 2.0 max |
| Si | 0.75 max |
| Cr | 16.0-18.0 |
| Ni | 6.0-8.0 |
| Mo | 0.6-0.9 |
| P | 0.03 max |
| S | 0.02 max |
| N | 0.2-0.3 |
| Fe | balance |
| W | 0.8-1.2 |

Blanzium (BX-1) was designed at W.L. Gore and Associates, Inc. (Flagstaff, Ariz.) and a laboratory sized ingot was made at Metalwerks in Aliquippa, Pa. The alloy was received in the form of a hot rolled plate with an approximate thickness of 0.100" and a weight of 5 lbs. The hot rolling temperature for this initial melt was selected to be 950° C. BX-1 is a multi-phase ferrous alloy where the predominant phase is austenite. This alloy was developed to have a corrosion resistance that is equivalent to 316L. This alloy was designed to have higher strength than 316L stainless steel and elastic recoil that is less than L605. Finally this alloy was designed to be non-magnetic. Table 2 describes the pitting resistance number (PREN) for both alloys. These numbers were calculated with the equations listed below and are represented on the Schaeffer diagram with the dashed lines in FIG. 11. Also included in Table 2 is the Pitting Resistance Number (PREN). The pitting resistance number is a calculated number based upon alloy additions and is a theoretical way of comparing corrosion resistance in stainless steels. The higher the PREN number typically the better the pitting corrosion resistance. Table 2 shows that the PREN number is very close to 316L and therefore theoretically should have an equivalent pitting resistance. The equation for PREN is below.

$$Cr_{eq} = Cr + Mo + (1.5*Si) + W$$

$$Ni_{eq} = Ni + (0.3*Mn) + (22*C) + (14.2*N)$$

$$PREN = Cr + 3.3(Mo + 0.5W) + 16N$$

TABLE 2

Pitting Resistance Number (PREN) for Blanzium and 316L (316)

| Cr Equivalent | 19.2 | Ni Equivalent | 12.2 | PREN (Blanzium) | 25.2 |
|---|---|---|---|---|---|
| Cr Eq Target | 19.5 | Ni Eq Target | 12 | PREN (316) target | 24 |

Figure 11:
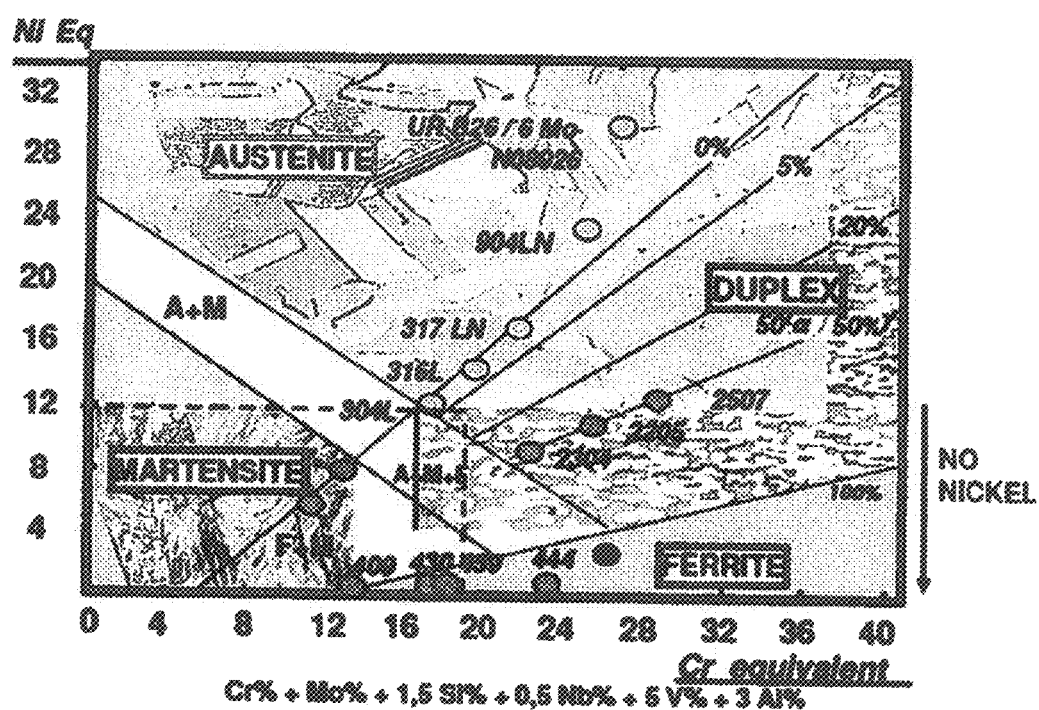
FIG. 11 shows a Schaefer Diagram used to predict the microstructure of the alloy.

FIG. 11 shows a Schaefer Diagram used to predict the microstructure of the alloy. This diagram indicates that based upon the chemistry that the volume fraction of ferrite should be around 5% or lower.

Figure 12:
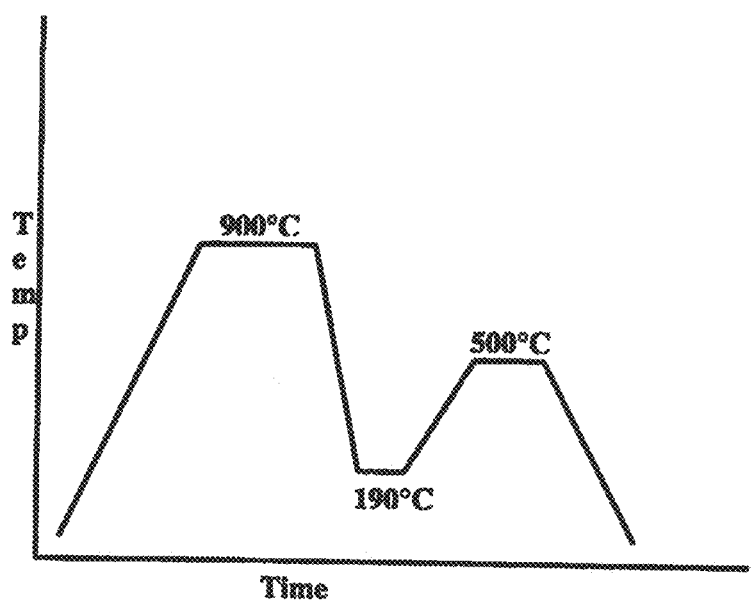
FIG. 12 shows show a schematic of the thermal profile from a quench and partitioning process.

Literature suggests that an annealing temperature of 900° C. favors the formation of austenite in steels and cooling rates seem to have an influence on the volume fraction of phases present in the microstructure. For this study an annealing time of 30 minutes was selected for all annealing condition. Cooling methods (rates) were varied by Water Quench (WQ, fast), Air Cool (AC, medium) and Quench and Partitioning (Q&P, slow). Water quenching was done in room temperature de-ionized water and air cooling was done in open ambient air. Q&P is a controlled quenching technique where after annealing at 900° C. the steel is quenched to a temperature of 190° C. in a fluidized sand bath and held for 120 seconds. The steel sample is then heated up to 500° C. in another fluidized bath and held for 10 seconds followed by water quenching. FIG. 12 show a schematic of the thermal profile from the Q&P process.

Figure 13:
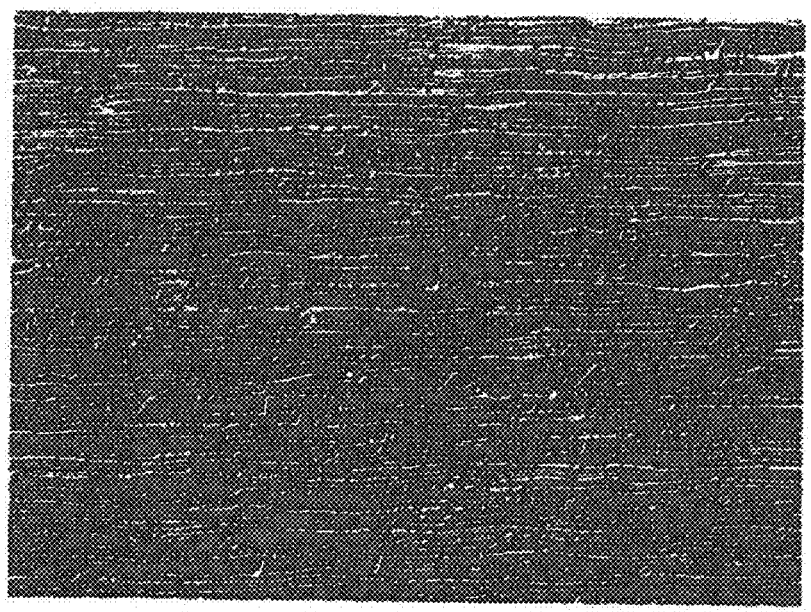
FIG. 13 shows the as-received microstructure of Blanzium after hot rolling.
Figure 14:
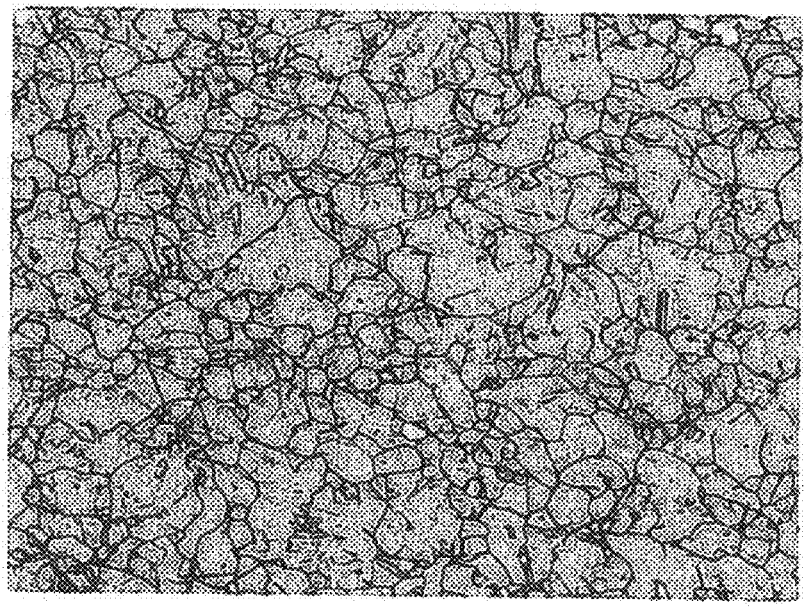
FIG. 14 shows a representative microstructure of Blanzium (BX-1) after annealing at 900° C. for 30 minutes (Q&P).

Samples from each cooling treatment were prepared for metallographic analysis which includes mounting each sample in Bakelite, grinding and polishing to a final 0.5 µm finish. After polishing and cleaning the samples are then etched in a solution of Microclean BS RD2-186 for 2 to 3 minutes. This etching solution revealed the microstructure. FIG. 13 shows the as-received hot rolled microstructure. This microstructure appeared to be a typical hot rolled fibered and banded microstructure. FIG. 14 shows a representative annealed microstructure. Overall, each cooling treatment revealed a similar microstructure which consisted of equiaxed grains through out the microstructure. Measurement of grain diameter taken from SEM images revealed a grain size that averaged (6 total measurements) to be 38.8

μm. This average grain size would correspond to an ASTM grain size of approximately 6.5.

Figure 15:
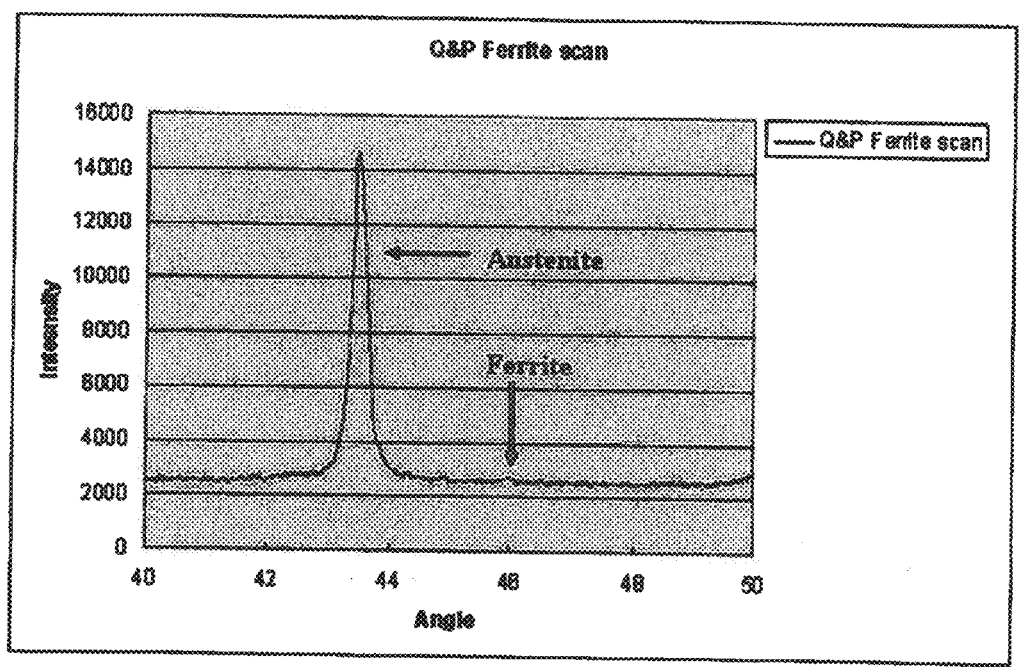
FIG. 15 shows X-Ray Diffraction measurements from Q&P treated samples. This measurement was done to determine volume fraction of the phases present

X-ray diffraction was done at Arizona State University using the PANalytical XpertPro MRD diffractometer and a Copper K alpha source. This equipment was used to determine the presence of phases present in the microstructure and volume fraction of these phases from each cooling treatment. FIG. 15 shows the XRD measurement taken from the Q&P treated sample and Table 3 shows the results of the volume fraction of ferrite measured from each sample. Overall the Q&P treatment was the best treatment for preserving the ferrite through the microstructure.

TABLE 3

Results from the XRD measurements for all the cooling treatments

| | Volume fraction Ferrite | |
|---|---|---|
| Sample | Transverse | Longitudinal |
| Water Quenched | 0 | 0 |
| Air Cooled | <1% | 0 |
| Q&P | <1% | <1% |
| As received | <1% | <1% |

In order to test the magnetic behavior of the alloy a Neodymium Magnet was placed on the as received and heat treated sample groups. A Neodymium magnet is a rare earth magnetic known to be one of the most powerful magnets and have been known to generate magnetic fields in excess of 1.4 Tesla. The Neodymium magnet did not stick to any of the sample groups and thus these materials are considered to be non-magnetic.

Figure 16:
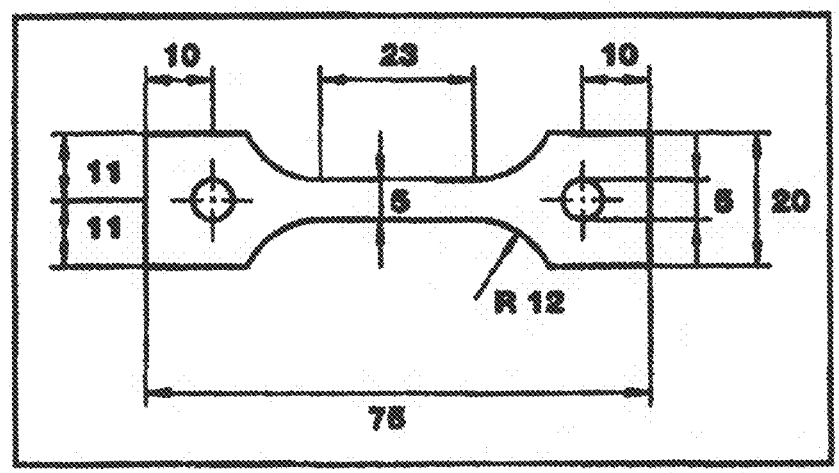
FIG. 16 shows a schematic used to manufacture tensile bars.

Tensile bars were made from the annealed BX-1 material for each cooling treatment. Tensile testing was done at Metcut Research in Cincinnati, Ohio. Four samples were tested in tension from each condition (12 total). These samples were tensile tested in accordance with ASTM E8 using a 1.0 inch extensometer and were tested at room temperature. FIG. 16 is a schematic drawing of the tensile bars that were used and Table 4 shows the results of the tensile testing for each cooling condition.

TABLE 4

Summary of average tensile results from all treatments, (n = 3 per condition)

| Specimen Identification | Condition | Mod (Msi) | UTS (ksi) | 0.2% YS (ksi) | Elong. (%) |
|---|---|---|---|---|---|
| C1 | WQ | 157.7 | 859.5 | 589.5 | 65.0 |
| C2 | AC | 199.0 | 845.8 | 512.5 | 70.0 |
| C3 | Q&P | 203.8 | 857.2 | 576.9 | 67.0 |
| C4 | AR | 199.9 | 928.5 | 788.3 | 53.0 |

Figure 17:
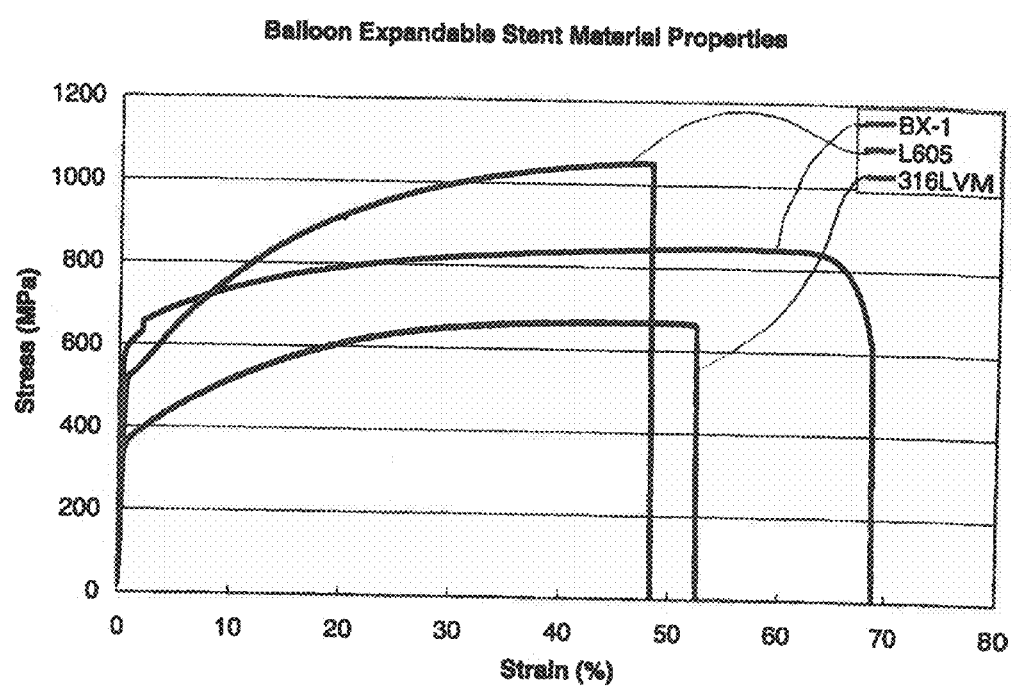
FIG. 17 shows stress-strain data from annealed BX-1 treated with Q&P process, annealed L605 tubing, and annealed 316L tubing. Laser cut strips from annealed tubing were used to tensile test the 316L and L605.

Overall, the samples processed with the Q&P process had the best combination of mechanical properties (high modulus, strength, and total elongation). FIG. 17 shows the stent strain curves of annealed L605 and 316L stent tubes compared to the annealed BX-1 material processed with the Q&P cooling treatment. Table 5 compares the modulus, yield strength (0.2% offset), ultimate tensile strength (UTS), and total elongation. The BX-1 material had a modulus and ultimate tensile strength that was between both stent materials. The yield strength and total elongation were greater than both 316L and L605 alloys.

TABLE 5

Comparison of stent alloys annealed L605, BX-1 (Q&P), and 316L.

| Material | Modulus (GPa) | UTS (MPa) | 0.2% YS (MPa) | Elong. (%) |
|---|---|---|---|---|
| L605 | 235 | 1079 | 567 | 56 |
| BX-1 | 204 | 857 | 577 | 67 |
| 316L | 193* | 661 | 340 | 53 |

*From P. Poncin and J. Proft, "Stent Tubing: Understanding the Desired Attributes," presented at Process for Medical Devices Conferences (Anaheim, CA) ASM International, Sep. 8-10, 2003.

Figure 18:
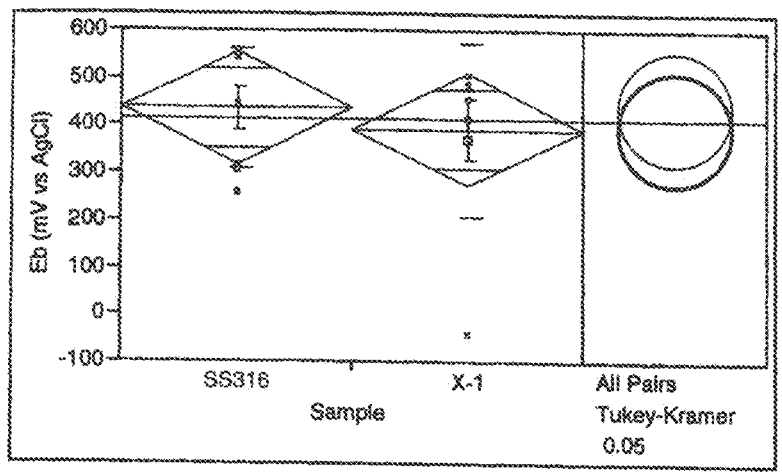
FIGS. 18A and B show results from Cyclic Potentiodynamic Polarization (CPP) testing showing statistical equivalence to 316L stainless steel in both pitting corrosion resistance (A) and uniform corrosion resistance (B).
Figure 18:
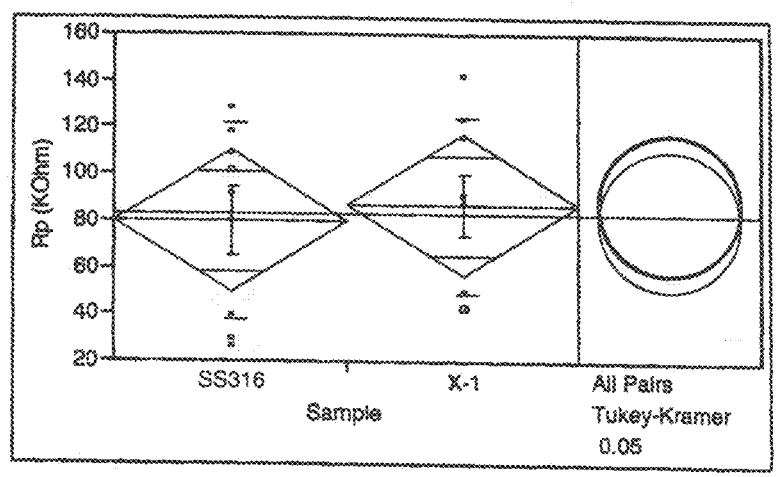

Corrosion testing was done in the form of Cyclic Potentiodynamic Polarization testing in PBS at room temperature open to air on both 316L sheet and the as-received hot rolled BX-1 alloy. The Gamry Potentiostat (model #7651) was used to test the alloys. Eight samples were prepared from each alloy. These samples were ground and mechanically polished to a 30 μm finish with a polycrystalline diamond paste. Both pitting and uniform corrosion resistance were determined from CPP plots. The data from these plots (both Eb and Rp, where Eb is breakdown potential and Rp is polarization resistance) were put in JMP and Tukey Kramer analysis was done. FIGS. 18A and 18B show that both alloys are statistically equivalent in pitting and uniform corrosion resistance.

Figure 19:
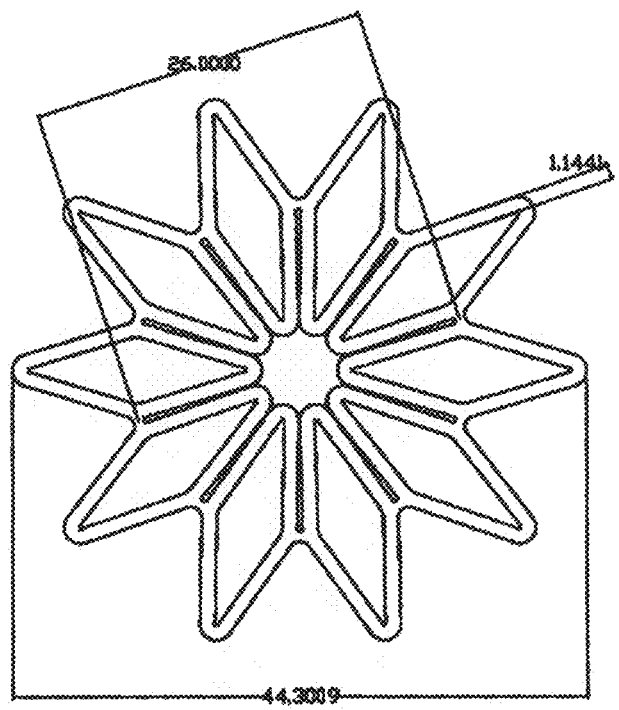
FIG. 19 shows a schematic drawing of stent ring cut from sheet materials 316, L605 and BX-1.
Figure 20:
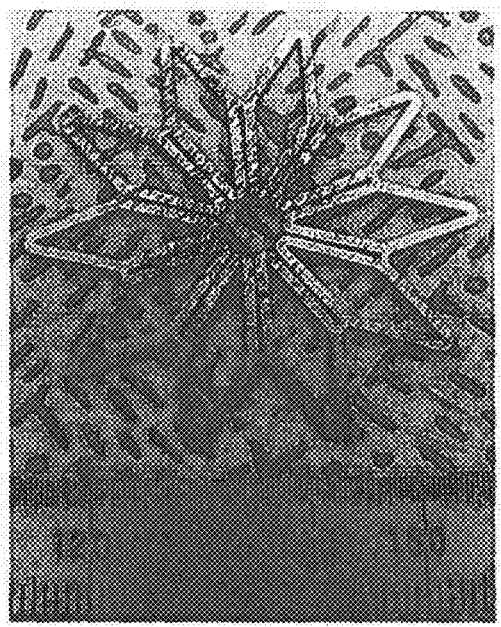
FIG. 20 shows the as cut ring from BX-1 alloy.
Figure 21:
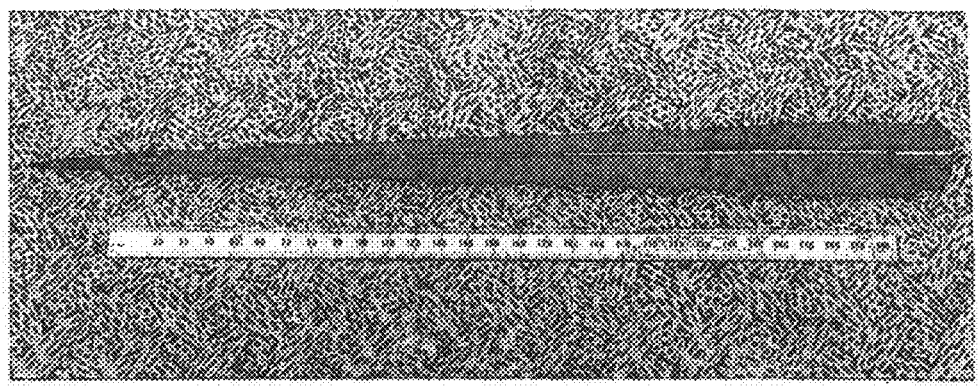
FIG. 21 shows the conical mandrel used to form stent rings.

A flat stent ring pattern was wire electrical discharge machined (EDM) from L605, 316L, and BX-1 sheet materials. FIG. 19 shows a schematic drawing of the stent ring materials. Each stent ring had a wall thickness of 0.014". FIG. 20 shows the as cut flat stent ring made from the BX-1 material. The stent rings were formed by sliding a 1" maximum diameter conical mandrel through the center of each flat stent ring at room temperature to create a cylindrical stent pattern. FIG. 21 shows the conical mandrel used to form stent rings from the three materials.

Figure 22:
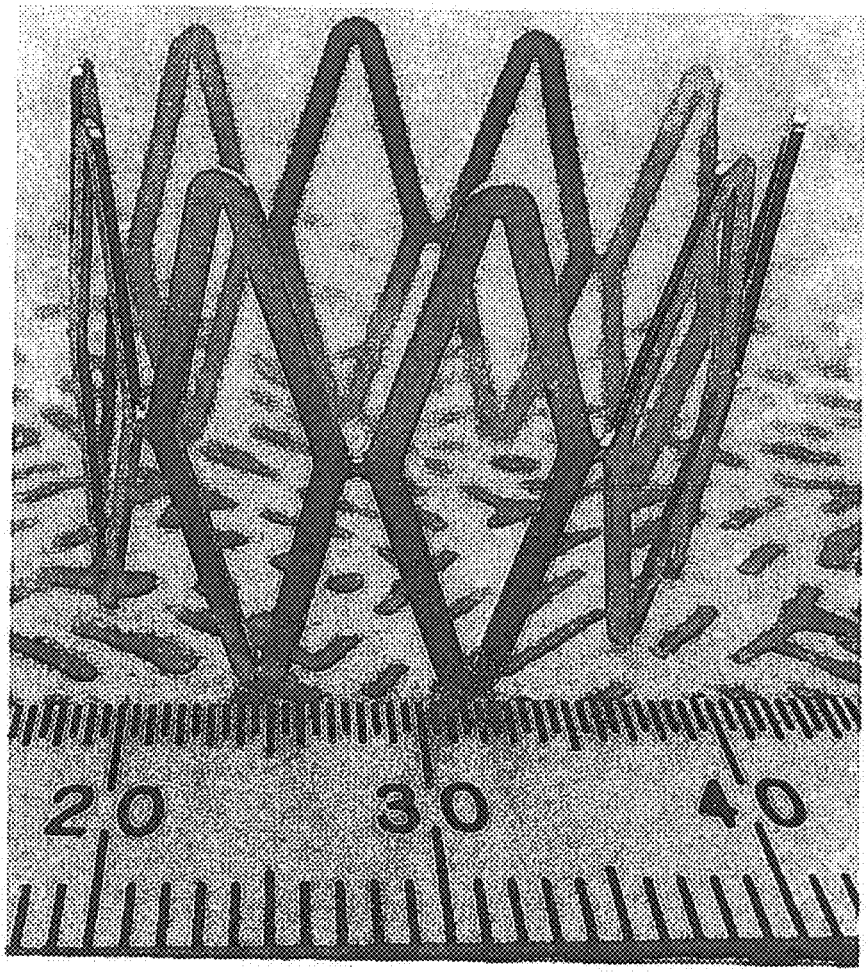
FIG. 22 shows the electropolished BX-1 stent ring.
Figure 23:
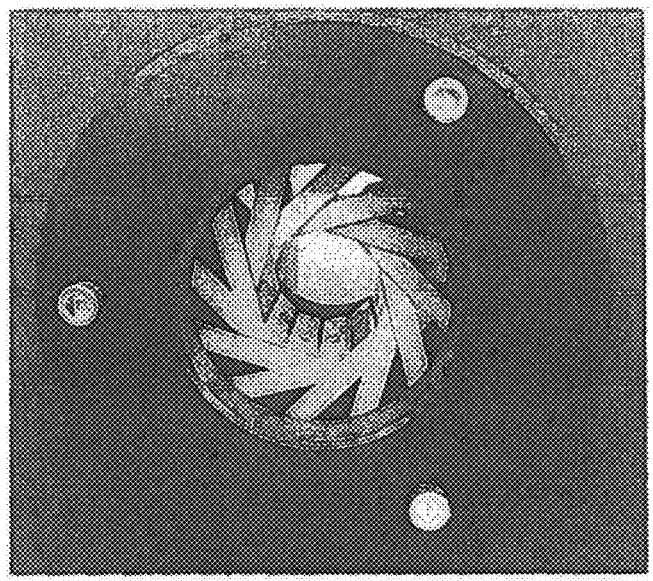
FIG. 23 shows the mechanical iris used to radially crush the stent rings.
Figure 24:
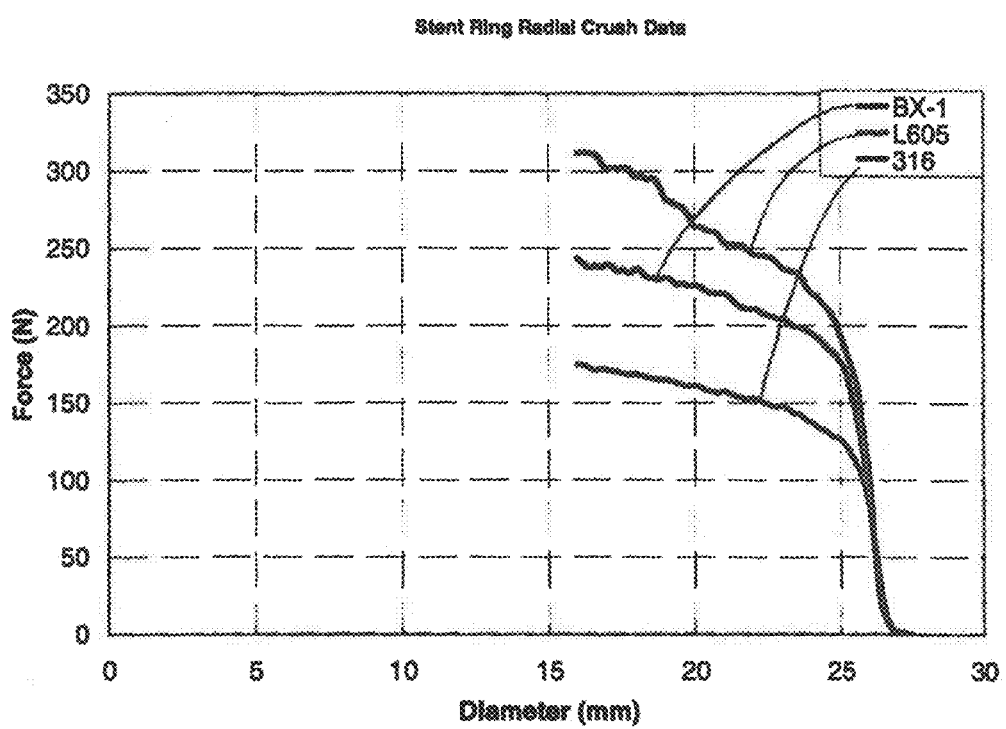
FIG. 24 shows the radial crush data from stent made from L605, 316L (316), and BX-1 materials.

Electropolishing (EP) was done on a BX-1 stent ring. FIG. 22 shows a formed and electropolished stent ring from the BX-1 material. The EP was done in multiple stages but removed 0.0005 inches of material per side. Polishing and etching was run using a current controlled power source Stent Rings were radially crushed in Radial Force machine #2001. This tester was fitted with 12 leaflets that form a mechanical iris that radially crushed the stent rings in order to compare radial strength. The mechanical iris started the test at a 30 mm diameter and crushed the rings to a 16 mm diameter. FIG. 23 shows the mechanical iris used to radially crush the stent rings. FIG. 24 compares the radial strength of the as cut stent rings made from BX-1, L605, and 316L (316). The BX-1 stent rings had a radial strength that was between the L605 and 316L alloys.

Figure 25:
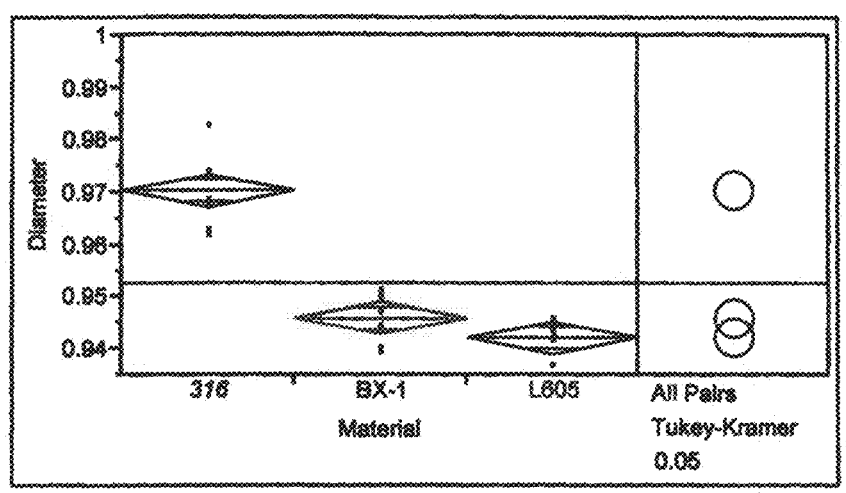
FIG. 25 shows recoil measured on L605, 316L (316), and BX-1 materials showing statistical equivalence between the BX-1 and L605 with a slight mean shift. Note, the closer the recoil values are to 1 inch indicates less recoil.

Recoil was measured from material after the stent rings were formed on the 1.0" tapered mandrel shown in FIG. 21. The inner diameter of each ring was measured in five locations optically using the Nikon vision system. Five diameters were measure in the inner diameter of each stent ring. Recoil was then determined by subtracting the mandrel diameter from each ring diameter. Table 6 shows the mean diameters measured from each stent ring material. The mean diameter of the BX-1 stent ring was between the L605 and 316L alloys. However, when the stent ring data was analyzed in JMP using a Tukey-Kramer analysis (FIG. 25) the L605 and BX-1 were statistically equivalent while the 316L alloy had statistically less recoil than the other two alloys.

TABLE 6

Recoil measured from each stent rings material.

| MATERIAL | MEAN DIAMETER (INCHES) | MEAN RECOIL (INCHES) |
|---|---|---|
| 316L | 0.97 | 0.03 |
| BX-1 | 0.95 | 0.05 |
| L605 | 0.94 | 0.06 |

Figure 26:
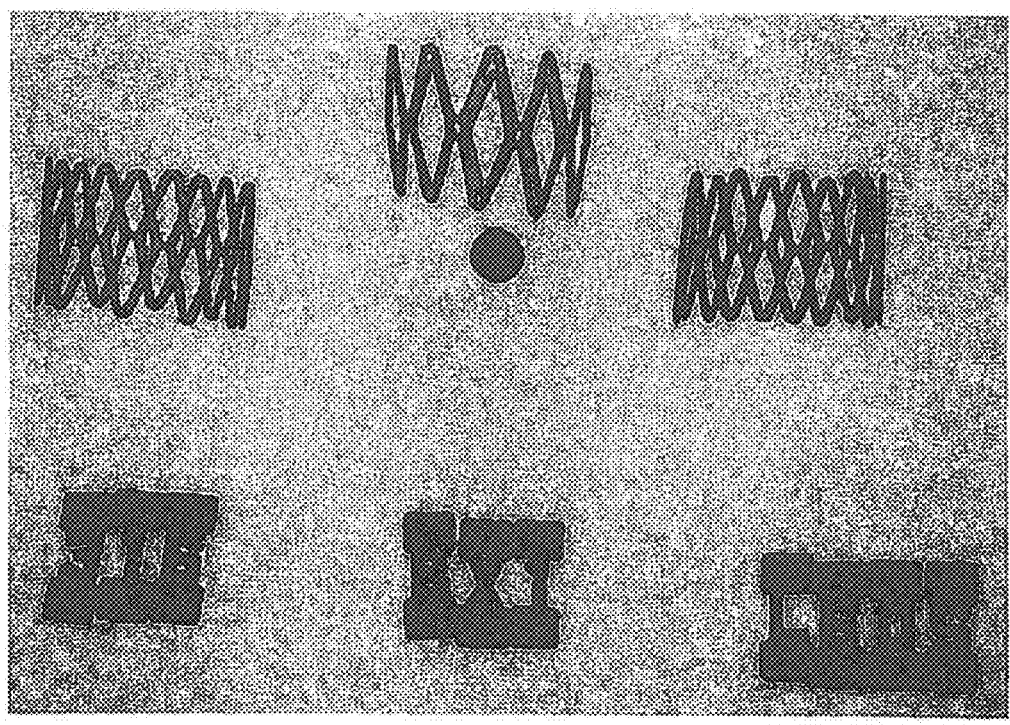
FIG. 26 shows fluoroscopy images taken of the three stent materials L605, 316L (316), and BX-1

Fluoroscopic images of the three stent materials were taken on the Phillips BV Pulsera Fluoro and X-Ray system. The BX-1 material appeared to be equivalent to the 316L stainless steel in radiopacity. The L605 stent appeared to be slightly darker than the 316L and BX-1 materials. FIG. 26 shows the fluoroscopy images taken of the three stent materials.

In addition to being directed to the embodiments described above and claimed below, the present invention is further directed to embodiments having different combinations of the features described above and claimed below. As such, the invention is also directed to other embodiments having any other possible combination of the dependent features claimed below.

Numerous characteristics and advantages of the present invention have been set forth in the preceding description, including preferred and alternate embodiments together with details of the structure and function of the invention. The disclosure is intended as illustrative only and as such is not intended to be exhaustive. It will be evident to those skilled in the art that various modifications may be made, especially in matters of structure, materials, elements, components, shape, size and arrangement of parts within the principals of the invention, to the full extent indicated by the broad, general meaning of the terms in which the appended claims are expressed. To the extent that these various modifications do not depart from the spirit and scope of the appended claims, they are intended to be encompassed therein.

What is claimed is:

1. A method of making an endoprosthesis comprising the steps of forming a flat sheet of multiphase stainless steel alloy into a desired shape, forming said desired shape into a tubular form, crimping said tubular form onto a balloon based endovascular delivery system, delivering said desired shape to an area of treatment and expanding said desired shape at the area of treatment, wherein the multiphase stainless steel alloy including austenite and ferrite phases, the multiphase stainless steel alloy comprising iron, chromium, nickel, tungsten, molybdenum, nitrogen, carbon, silicon, and manganese, wherein the multiphase stainless steel alloy consists of iron, 16.0-18.0 wt % chromium, 6.0-8.0 wt % nickel, 0.8-1.2 wt % tungsten, 0.6-0.9 wt % molybdenum, 0.2-0.3 wt % nitrogen, at most 2.0 wt % manganese, at most 0.75 wt % silicon, at most 0.03 wt % carbon, at most 0.03 wt % phosphorus, and at most 0.02 wt % sulfur, wherein the multiphase stainless steel alloy has a volume fraction of ferrite of 5% or lower.

2. A method of making an endoprosthesis comprising the steps of forming a tubular form of multiphase stainless steel alloy into a desired shape, crimping said tubular form onto a balloon based endovascular delivery system, wherein the multiphase stainless steel alloy includes austenite and ferrite phases, wherein the multiphase stainless steel alloy comprising iron, chromium, nickel, tungsten, molybdenum, nitrogen, carbon, silicon, and manganese, wherein the multiphase stainless steel alloy consists of iron, 16.0-18.0 wt % chromium, 6.0-8.0 wt % nickel, 0.8-1.2 wt % tungsten, 0.6-0.9 wt % molybdenum, 0.2-0.3 wt % nitrogen, at most 2.0 wt % manganese, at most 0.75 wt % silicon, at most 0.03 wt % carbon, at most 0.03 wt % phosphorus, and at most 0.02 wt % sulfur, wherein the multiphase stainless steel alloy has a volume fraction of ferrite of 5% or lower.

3. A method of making an endoprosthesis comprising the steps of forming a wire of multiphase stainless steel alloy into a desired tubular shape, crimping said tubular shape onto a balloon based endovascular delivery system, delivering said desired shape to an area of treatment, and expanding said desired shape at the area of treatment, wherein the multiphase stainless steel alloy includes austenite and ferrite phases, wherein the multiphase stainless steel alloy comprises iron, chromium, nickel, tungsten, molybdenum, nitrogen, carbon, silicon, and manganese, wherein the multiphase stainless steel alloy consists of iron, 16.0-18.0 wt % chromium, 6.0-8.0 wt % nickel, 0.8-1.2 wt % tungsten, 0.6-0.9 wt % molybdenum, 0.2-0.3 wt % nitrogen, at most 2.0 wt % manganese, at most 0.75 wt % silicon, at most 0.03 wt % carbon, at most 0.03 wt % phosphorus, and at most 0.02 wt % sulfur, wherein the multiphase stainless steel alloy has a volume fraction of ferrite of 5% or lower.

4. The method of claim 3 further comprising the steps of impacting the formed device with a media to impart compressive residual stresses at the surface of the metal.

5. The method of claim 3 further comprising the step of electropolishing the formed device prior to crimping said tubular form onto a balloon based endovascular delivery system.

* * * * *